(12) United States Patent
Sengupta et al.

(10) Patent No.: US 7,033,076 B2
(45) Date of Patent: Apr. 25, 2006

(54) METHOD OF STABILIZING AN X-RAY SOURCE OF AN ELECTRON BEAM TOMOGRAPHY SYSTEM

(75) Inventors: Souma Sengupta, Belmont, CA (US); Paul Magnuson, Hillsborough, CA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 342 days.

(21) Appl. No.: 10/649,159

(22) Filed: Aug. 27, 2003

(65) Prior Publication Data

US 2005/0047548 A1   Mar. 3, 2005

(51) Int. Cl.
*G01D 18/00*   (2006.01)

(52) U.S. Cl. .................. 378/207; 378/205; 378/137

(58) Field of Classification Search ............... 378/4, 378/12, 16, 113, 137, 138, 146, 205, 207; 250/252.1
See application file for complete search history.

(56) References Cited

U.S. PATENT DOCUMENTS

| 4,352,021 A | 9/1982 | Boyd et al. ............ 378/12 |
| 5,442,673 A | 8/1995 | Rand et al. ............ 378/10 |

*Primary Examiner*—David V. Bruce
*Assistant Examiner*—Courtney Thomas
(74) *Attorney, Agent, or Firm*—McAndrews, Held & Malloy, Ltd.; Peter J. Vogel; Michael A. Dellapenna

(57) ABSTRACT

A method of calibrating an electron beam tomography (EBT) system includes determining a change in x-ray intensity for detecting elements in each detector array through multiple imaging sweeps during an initial activation of the EBT system, deriving scale factors based on the determined changes in x-ray intensity for the imaging sweeps, and using the scale factors to modify a trajectory and deflection of the electron beam during the multiple imaging sweeps to maintain constant x-ray intensity on each detector array.

23 Claims, 4 Drawing Sheets

METHOD OF STABILIZING AN X-RAY SOURCE OF AN ELECTRON BEAM TOMOGRAPHY SYSTEM

BACKGROUND OF THE INVENTION

The present invention generally relates to electron beam tomography (EBT) systems, and more particularly to a method of adjusting electron beam deflection in order to stabilize relative x-ray intensities between detector rings in EBT systems.

Computerized tomography (CT) systems produce planar images along imaginary cuts, or slices, through a patient. CT systems typically include an x-ray source, which revolves about an imaginary axis through a subject. After passing through the subject, the x-rays impinge on an opposing array of detectors.

Typical CT patient scans are executed in either an axial mode or in a helical mode. In axial mode, the table that supports the patient stops, the scan is executed, and then the table moves to a new location. In helical mode, the patient table continuously moves throughout the course of the scan. Single slice scanners (scanners having one detector array) are common, and dual slice CT systems (systems having two detector arrays) are known.

Some CT scanners include a scanning electron beam x-ray source, such that an electron beam is magnetically deflected so as to rotate in a generally arcuate path, and in doing so, impinges upon an arc-shaped target. As the electron beam impinges on the target, a source of x-rays is generated. As the electron beam moves, so does the source of x-rays. The x-rays encounter a collimator that passes a portion and blocks a portion of the x-rays. The x-rays are shaped into a fan beam by the collimator and then intercepted by a ring-shaped detector array on an opposite side of the patient. U.S. Pat. No. 4,352,021 ("the '021 patent"), issued Sep. 28, 1982, discloses such an electron beam scanner.

With respect to dual detector arrays, the quality of images typically depends, at least in part, upon the position of the x-ray beam spot on the target. Typically, with dual detector arrays, it is desired to maintain uniform x-ray intensity on both detector arrays. Movement of the beam spot on the target affects the x-ray intensity on each detector. The beam spot may move due to several reasons including deformation of the target. For example, the deformation of the target with increased imaging sweeps causes the beam spot to move relative to the target. As the beam spot moves, or shifts, on the target, the resulting x-ray fan beam shifts in response thereto. As the x-ray fan beam shifts, each detector array that detects the x-ray fan beam receives more or less of the x-ray fan beam, depending on the nature of the shift. Consequently, the x-ray intensity on one detector array typically differs from the other detector array when the x-ray beam spot moves, or shifts, relative to the target.

Various phenomena may cause the beam spot to move relative to the target, including target deformation caused by thermal effects, eddy currents, and the like. As a scan progresses through multiple sweeps, the shifting effect of the beam spot relative to the target typically increases. Consequently, the position of the beam spot on the target at a particular point varies from sweep to sweep. As the beam spot moves, the x-ray fan beam is displaced with respect to the detector arrays and the resultant x-ray intensities on the detectors arrays varies, thereby producing images of varying quality, particularly at the end of long scans.

FIG. 1 illustrates an axial cross-sectional view of an electron beam tomography ("EBT") system 100. The EBT system 100 includes a target ring 112 onto which an electron beam impinges at a beam spot 114, thereby producing an x-ray fan beam 116 that is detected by detector arrays 118. The electron beam may be rotated from one end 120 of the target ring 112 to the other end 122 of the target ring 112 through a semi-circular arc defined by the target ring 112. One "sweep" is typically defined by movement of the electron beam from one end 120 to the other end 122 of the target ring 112. With each passing sweep, however, the target ring 112 gradually deforms. The effect of deformation after numerous sweeps is shown by expanded ring 124, the shape of which is exaggerated for illustrative purposes. The effect of the deformation compounds with each passing sweep. Thus, after a large number of sweeps, the target ring 112 may be substantially deformed. As the target ring 112 deforms with each sweep, the resulting electron fan beam shifts, resulting in unequal x-ray intensities on the detectors.

Thus, a need exists for a method that ensures that the x-ray intensities on both detector arrays remain constant in order to provide consistent, high quality images.

BRIEF SUMMARY OF THE INVENTION

Embodiments of the present invention provide a method of stabilizing an x-ray source of an electron beam tomography (EBT) system, in which an electron beam impinges upon a target ring at a beam spot that produces an x-ray fan beam detected by a plurality of detector arrays. The method includes determining the ratios of the x-ray intensities for each of the corresponding elements of the detector arrays for a series of sweeps following an initial activation of the EBT system.

The method also includes estimating a change in position of the electron beam position on the target based on the determining step. The next step in the method is to derive corresponding scale factors based on the determined change in x-ray intensity ratios for each imaging sweep. Subsequently, at least one of a trajectory and deflection of the electron beam during multiple imaging sweeps are modified based on the derived scale factors for each imaging sweep to ensure that the corresponding beam spot maintains substantially the same position in the axial direction of the target ring through multiple sweeps. The method may ensure that x-ray intensities on the detector arrays are uniform and constant through the multiple imaging sweeps.

Figure 1:
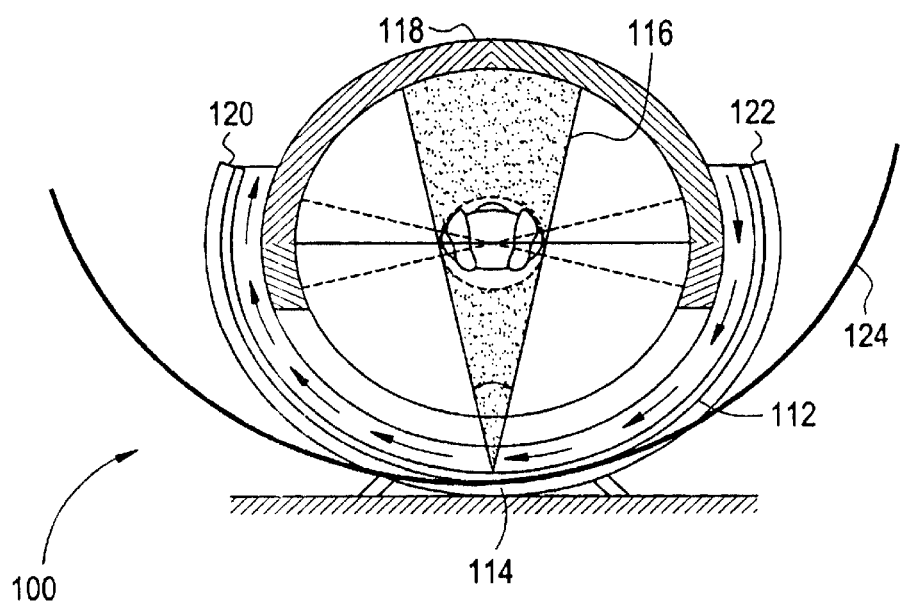
FIG. 1 illustrates a side view of an electron beam tomography ("EBT") system.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

Figure 2:
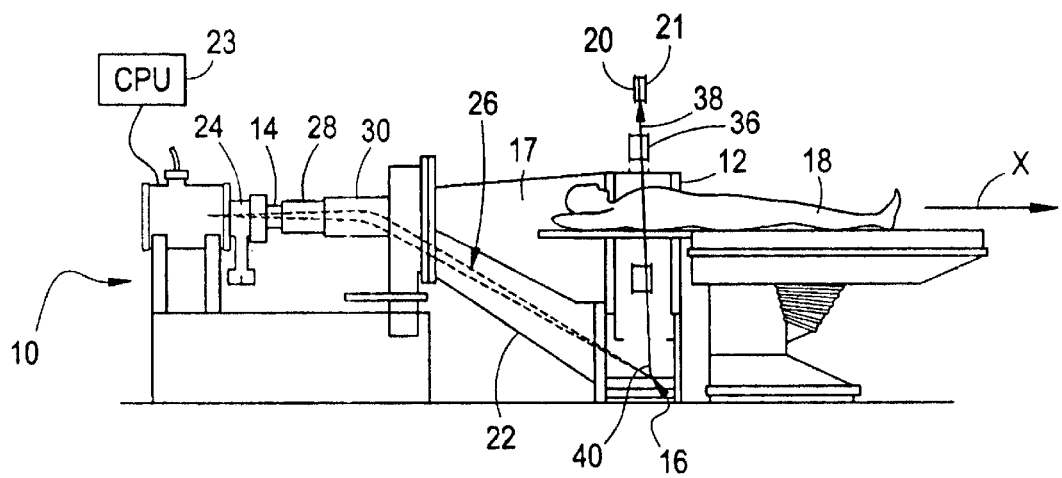
FIG. 2 illustrates a transverse cross-sectional view of an electron beam tomography ("EBT") system, according to an embodiment of the present invention.

FIG. 2 illustrates a side view of an electron beam tomography ("EBT") system 10, according to an embodiment of the present invention. The EBT system 10 includes an electron beam scan tube 12 having a cylindrical portion 14 and a semi-circular conical portion 17; and x-ray detector arrays 20 and 21. Each of the detector arrays 20 and 21 has a plurality of detecting elements configured to receive and detect x-rays. The scan tube 12 develops and projects an electron beam 26 towards a semi-circular ring-shaped target ("target ring") 16. The target ring 16 generates x-rays at portions thereof where the electron beam 26 impinges. The x-rays, after being collimated and subsequently passed through the patient 18 lying along a patient axis denoted by line X, are intercepted and detected by the detector arrays 20 and 21. A data output of the detector array 20 and 21 is processed by a central processing unit 23, which controls operation of the EBT system 10, to form diagnostic images and other information of interest to a physician and the patient.

Scan tube 12 includes a vacuum envelope 22, which houses an electron gun 24 in the cylindrical portion 14. The electron gun 24 projects the axial electron beam 26 through the semi-circular conical portion 17. Focus coils 28 magnetically focus the electron beam 26 to a beam spot 40, which impinges on the target ring 16. Bending coils 30 provide a magnetic field to bend the electron beam 26 so that it is directed through the semi-circular conical portion 17 toward the target ring 16.

The bending coils 30 not only deflect the electron beam 26, but also rapidly and repeatedly sweep the electron beam 26 arcuately along the target ring 16 so as to create a source of x-rays that rotates substantially within a single plane. A collimator assembly 36 is disposed in the beam path between the target ring 16 and the detector arrays 20 and 21 so as to block the unwanted x-rays emitted by the target ring 16 and to define an x-ray beam projected as a planar fan beam (shown below with respect to FIG. 3). A sector of the x-ray fan beam is detected by a portion of the x-ray detector arrays 20 and 21, which provide measured values to the central processing unit 23 in response thereto.

Figure 3:
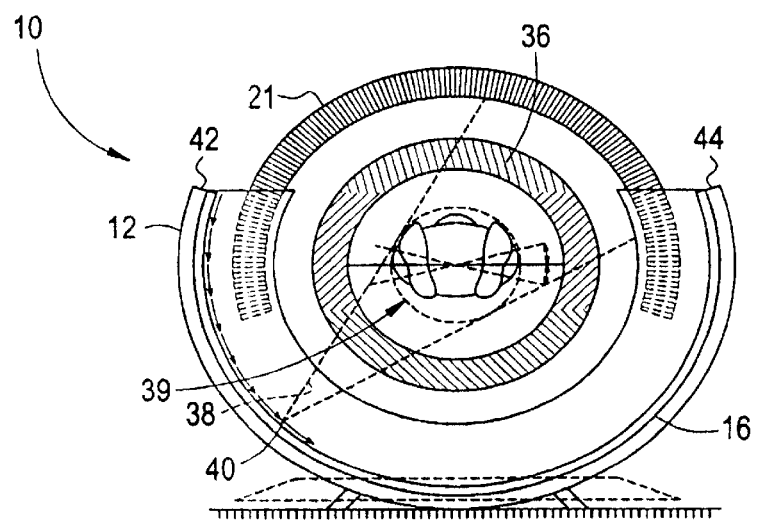
FIG. 3 illustrates an axial cross-sectional view of an electron beam tomography ("EBT") system, according to an embodiment of the present invention.

FIG. 3 illustrates an axial cross-sectional view of the EBT system 10. By way of example, the collimator assembly 36 may be donut or circular shaped to surround the scan field 39. The collimator assembly 36 collimates x-rays projecting from the target ring 16 and projecting onto the detector arrays 20 and 21. As shown in FIG. 3, only detector array 21 is visible, as detector array 20 is positioned behind and adjacent to detector array 21. The x-ray fan beam 38 is shown emanating from the beam spot 40. That is, the electron beam 26 impinges on the target ring 16 at the beam spot 40, which in turn generates the x-ray fan beam 38. The electron beam 26 may be swept from a first end 42 of the target ring 16 to a second end 44 of the target ring 16. As mentioned above, however, the target ring 16 gradually deforms with each passing sweep resulting in a variable detection of the x-ray fan beam 38 by the detector arrays 20 and 21.

Figure 4:
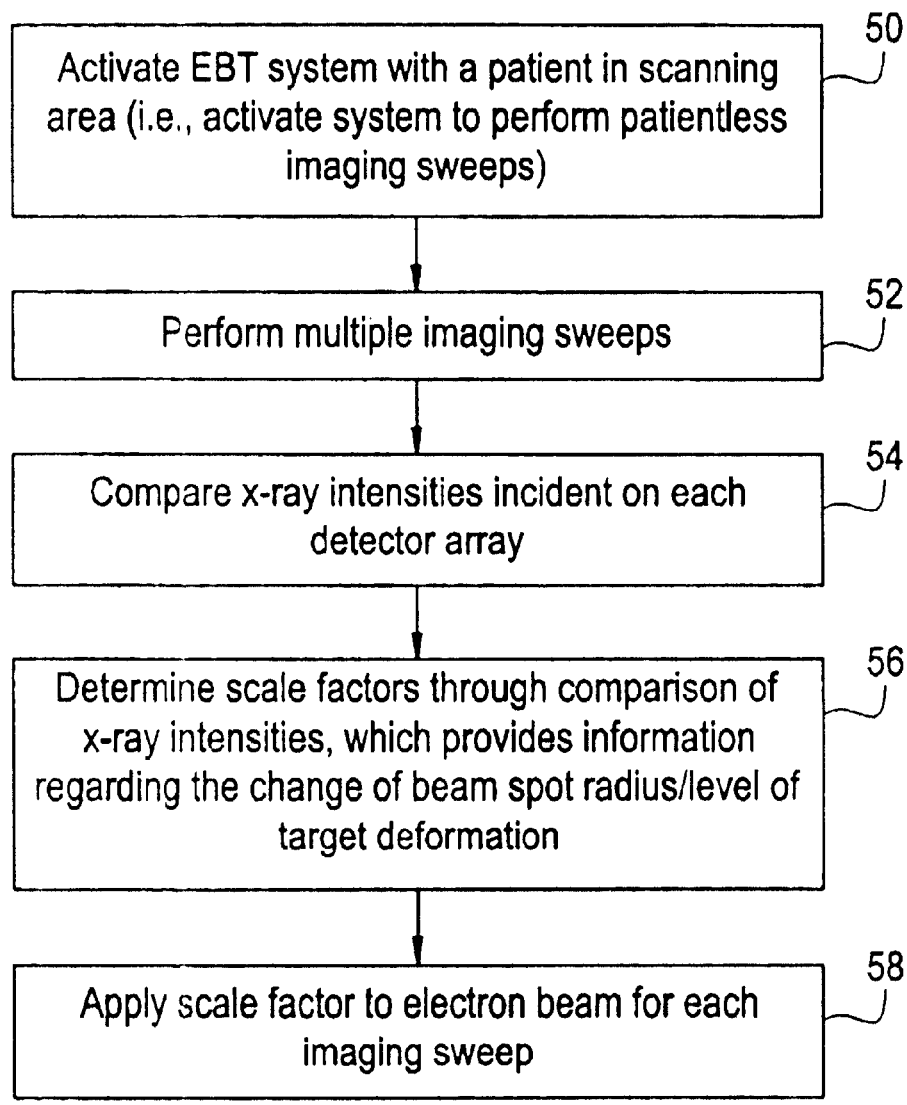
FIG. 4 is a flow chart illustrating a method of maintaining uniform x-ray intensity upon two detector arrays, according to an embodiment of the present invention.

FIG. 4 is a flow chart illustrating a method of maintaining uniform x-ray intensity upon two detector arrays, such as detector arrays 20 and 21, according to an embodiment of the present invention. FIG. 4 is a flow chart of a process of stabilizing the x-ray intensity in the EBT system 10. At 50, the EBT system 10 is activated without a patient in the scanning area. That is, the EBT system 10 performs an imaging procedure without a patient in the scanning area. The initial activation is performed after the EBT system 10 is assembled and operational. Optionally, the activation, and subsequent steps below, may occur at periodic times to ensure consistent x-ray intensity upon the detector arrays 20 and 21. At 52, the EBT system 10 performs multiple imaging sweeps.

Figure 5:
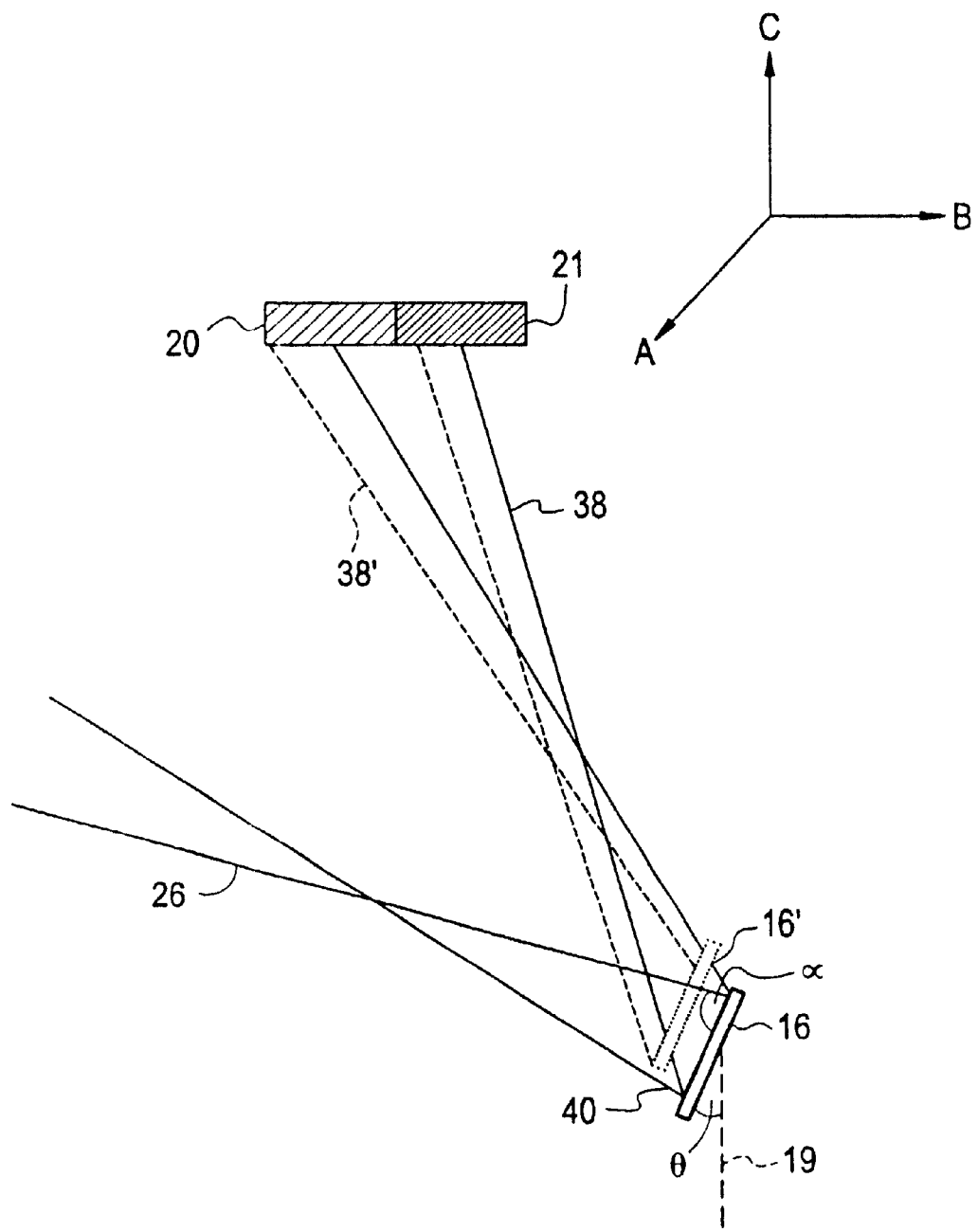
FIG. 5 illustrates a partial transverse cross-sectional view of the effects of a deforming target ring.

FIG. 5 illustrates a partial transverse cross-sectional view of the effects of a deforming target ring 16' after multiple imaging sweeps. At the beginning of a scan, an electron beam 26 impinges the target ring 16 at the beam spot 40, resulting in an x-ray fan beam 38. As shown in FIG. 5, an equal portion of the x-ray fan beam 38 is detected by the detector array 20 and the detector array 21. However, as the scan progresses through multiple imaging sweeps, the target ring 16 deforms due to temperature variation resulting in a deformed target ring 16'. That is, the target ring 16' is oriented, angled, or otherwise situated differently than the original position of the target ring 16. The electron beam 26 impinges on the deformed target ring 16' at a different position due to the fact that the orientation of the target ring 16' is different as compared to the target ring 16 because of the gradual deformation of the target ring 16 with each additional sweep. The resulting x-ray fan beam 38' contacts the detector arrays 20 and 21 in unequal portions. That is, as shown in FIG. 2, the detector array 20 receives a greater proportion of the x-ray fan beam 38', and therefore, a higher intensity of x-rays, as compared to the detector array 21.

Referring again to FIG. 4, at 54, the central processing unit 23 compares the x-ray intensities incident on each detector array 20 and 21. The comparison of x-ray intensities, or changes in x-ray intensities, for each sweep, determines the amount of change in the position of the x-ray fan beam for each sweep. For example, if the x-ray intensity on detector array 20 becomes greater than that of detector array 21, a determination is made that x-ray fan beam 38 is moving or shifting such that more of the x-ray fan beam 38 is upon x-ray detector array 20. The x-ray fan beam 38 shifts due to the fact that the target ring 16, upon which the beam spot 40 impinges, is deforming. As the target 16 deforms, the radius of the beam spot 40 changes due to the fact that the location of the target 16 changes upon deformation. Hence, the angle of incidence a of the electron beam 26, which, along with the location of the target 16, defines the position of the beam spot 40, changes upon deformation of the target 16, thereby varying the radius of the beam spot 40. Consequently, the x-ray intensity detected by detectors within the detector arrays 20, 21 varies because the radius of the resulting x-ray fan beam 38 that emanates from the beam spot 40 changes, producing varying degrees of x-ray intensities for different detectors within the detector arrays 20, 21.

Thus, a determination of the change of x-ray intensities on the detector arrays 20, 21 provides information regarding the deformation of the target ring 16. There is a direct correlation between the deformation of the target ring 16 and the movement of the x-ray fan beam 38 upon the detector arrays 20, 21. Further, there is a direct correlation between the deformation of the target ring 16 and the location of the beam spot 40 on the target ring 16. The location of the beam spot 40 varies depending on the changing nature, or deformation, of the target ring 16, which affects the intersection of the electron beam 26 and the target ring 16.

The following formulae may be used to estimate the change in the radius of the beam spot 40:

$$\Delta_r = k(1 - \sqrt{2(I_a/(I_b+I_a))}); \quad (1)$$

and $$k = S(W/\tan \Theta)(C_s/C_d), \quad (2):$$

where:

$\Delta_r$=the change in the radial position of the beam spot 40 on the target ring 16;

$I_a$=the smaller (i.e., less intense) of the two signals from the detector arrays 20 or 21;

$I_b$=the larger (i.e., more intense) of the two signals from the detector arrays 20 or 21;

S=−1 if $I_a$ is on detector array 20, or 1 if $I_a$ is on detector array 21 (or vice versa);

W=the detector exposure halfwidth;

Θ=the angle of a target ring 16 with respect to a vertical plane 19, as shown in FIG. 5 (i.e., a plane that is perpendicular to a plane of a surface that supports the EBT system 10);

$C_s$=the distance between the collimator 36 and the beam spot 40; and $C_d$=the distance between the collimator 36 and the detector arrays 20, 21.

The formulae listed above are only examples. Different formulae may be used depending on the configuration of a particular EBT system.

Table I shows typical examples of changes in the radius (in mm) of the beam spot 40 at various sweeps of the electron beam 26 of the EBT system 10 due to deformation of the target ring 16 for a series of detectors in the detector arrays 20, 21.

TABLE I

| Detector | Sweep 60 | Sweep 120 | Sweep 180 | Sweep 240 | Sweep 300 |
| --- | --- | --- | --- | --- | --- |
| 250 | 0.276018 | 0.363864 | 0.256662 | 0.26221 | −0.1044 |
| 500 | 0.185432 | 0.258742 | 0.13474 | 0.26802 | −0.19213 |
| 750 | −0.72333 | −1.01883 | −1.33968 | −1.62728 | −1.58469 |
| 1000 | −0.44604 | −0.86554 | −1.04132 | −1.10313 | −1.22496 |
| 1250 | −0.19269 | −0.44078 | −0.46922 | −0.40012 | −0.42527 |
| 1500 | 0.789633 | 1.102902 | 1.366293 | 1.492749 | 1.847374 |

At 56, scale factors, which are based on the radius changes of the beam spot 40 and, therefore, the levels of target deformation, for each sweep (e.g., changes in beam spot radius), are then determined to compensate for the amount of target deformation for each sweep. The following formula may be used to calculate the scale factors:

$$F = (R_s + D\Delta_r)/R_s, \text{where:}$$

D=a dampening factor (<1);

$R_s$=the radius of the beam spot 40 for a particular sweep; and $\Delta_r$=the change in radial position of the beam spot 40 on the target ring 16.

The formula listed above is only an example. A different formula may be used depending on the configuration of a particular EBT system.

The scale factors are used to modify the deflection of the electron beam 26 to offset the amount of target deformation/beam spot radius change. The electron beam 26 may be shifted in a corresponding direction in order to offset the deformation and/or shifting of the target ring 16. The scale factors are used to ensure that the trajectory and/or deflection of the electron beam 26 is modified so that the beam spot 40 on the target ring 16 maintains the same angular position with respect to the detecting surfaces of the detector arrays 20 and 21 through multiple imaging sweeps so that x-ray intensities on the detector arrays 20 and 21 are within acceptable limits for a desired quality of images. That is, the beam spot 40 remains in a constant position with respect to the detector arrays as the electron beam 26 is rotated through the arc of the target ring 16.

The central processing unit 23 controls a deflection system, including the focus coils 28 and bending coils 30 discussed above with respect to FIG. 3, to modify the trajectory and deflection of the electron beam 26 for each imaging sweep based on currents through the coils. Dipole coil currents are modified according to the scale factors and applied to the deflection system including the focus coils 28 and the bending coils 30 in order to steer the electron beam 26 to a position where the x-ray intensities on the detector arrays 20 and 21 are constant with respect to one another.

Referring again to FIG. 4, at 58, the scale factors are applied to the electron beam 26 for each sweep. For each sweep, a set of several different scale factors is determined. For a first sweep, the deflection and/or trajectory of the electron beam 26 may not be modified. For the second sweep, a set of scale factors is used to modify the deflection of the electron beam 26. As stated above, the scale factors are determined by the change in x-ray intensities incident on the detector arrays 20, 21, which in turn provides information regarding the deformation of the target ring 16, which in turn provides information regarding the changes in radial location of the beam spot 40, for each imaging sweep. Overall, the modified deflection of the electron beam 26 for each imaging sweep based on the deformation of the target ring 16 for each respective imaging sweep ensures substantially constant x-ray intensity on each detector array 20, 21.

The sets of scale factors for each sweep of the EBT system 10 are stored within the central processing unit 23 and/or a computer diskette, CD ROM, or the like. Each time the EBT system 10 is used to image a patient, the stored scale factors are used to modify the trajectory and deflection of the electron beam 26 for each imaging sweep in order to maintain the angular position of the beam spot 40 on the target ring 16 during multiple imaging sweeps. Thus, the scale factors are applied to ensure that the x-ray intensities on the detector arrays 20, 21 remain constant through multiple imaging sweeps.

Using FIG. 5 as an example, embodiments of the present invention provide a method of shifting the electron beam 26 in directions defined by axes A, B, C in order to modify the deflection and trajectory of the electron beam 26 based upon the deformation of the target ring 16. The deflection and trajectory of the electron beam 26 is shifted, or otherwise modified, for each imaging sweep based on the set of scale factors for a particular imaging sweep so that the resulting electron fan beam is of substantially constant intensity on the detector arrays 20 and 21 for each sweep.

Because the scale factors for each sweep are stored within the central processing unit 23 or the like, the EBT system 10 may apply the scale factors during subsequent imaging procedures. The calibration process described above may be repeated on a regular basis, or at select times. For example, the calibration process may be repeated when the alignment of the collimator is changed, and/or when changes to the deflection and steering system occur.

Optionally, an operator may desire different x-ray intensities on the detector arrays. In that case, the method may determine appropriate scale factors that coincide with an operator's preferences. Also, alternatively, the method may be used with an EBT system that includes more or less than two detector arrays.

Thus, embodiments of the present invention provide a method for ensuring that x-ray intensities on both detectors of a multiple detector array EBT system remain constant in order to provide consistent, high quality images.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method of stabilizing an x-ray source of an electron beam tomography (EBT) system in which an electron beam impinges upon a target ring at a beam spot that produces an x-ray fan beam detected by a plurality of detector arrays, said method comprising:

determining changes in x-ray intensity for detecting elements in each detector array for a series of imaging sweeps during an initial activation of the EBT system;

deriving a set of scale factors based on the determined change in x-ray intensity for each imaging sweep; and modifying at least one of a trajectory and deflection of the electron beam during multiple imaging sweeps based on the derived scale factors for each imaging sweep to ensure that the corresponding beam spot maintains substantially the same angular position on the target ring, thereby ensuring that a resulting x-ray fan beam maintains the same position on the surfaces of the plurality of the detector arrays, through multiple imaging sweeps.

2. The method of claim 1, wherein said determining step comprises correlating the change in x-ray intensity for the detecting elements in each detector array with a deformation of the target ring during each imaging sweep.

3. The method of claim 2, wherein said determining step further comprises determining changes in the electron beam on the target through the correlation of the deformation of the target ring.

4. The method of claim 3, wherein said determining step further comprises estimating the change in radial position of the beam spot on the target ring using the following formulae:

$$\Delta_r = k(1 - \sqrt{(2(I_a/(I_b+I_a))}); \text{ and} \quad (1)$$

$$k = S(W/\tan \Theta)(C_s/C_d), \text{ where:} \quad (2)$$

$\Delta_r$=the change in the radial position of the beam spot on the target ring;
$I_a$=the smaller of the two signals from the detector arrays;
$I_b$=the larger of the two signals from the detector arrays;
S=−1 if $I_a$ is on a first detector array, or 1 if $I_a$ is on a second detector array;
W=the detector exposure halfwidth;
Θ=the angle of a target ring with respect to a vertical plane;
$C_s$=the distance between a collimator and the beam spot; and $C_d$=the distance between the collimator and the detector arrays.

5. The method of claim 4, wherein said deriving step comprises deriving the scale factors using the following formula:

$$F = (R_s + D \Delta_r)/R_s, \text{ where:}$$

D=a dampening factor; and
$R_s$=the radius of the beam spot for a particular sweep.

6. The method of claim 1, ftuther comprising storing the scale factors fur use in subsequent imaging procedures.

7. The method of claim 1, wherein the scale factors are different for each imaging sweep.

8. The method of claim 1, further comprising maintaining a uniform and constant x-ray intensity on each detector anay due to said modifying step.

9. The method of claim 8, wherein the x-ray intensity on each detector array is the same.

10. A method of stabilizing an x-ray source of an electron beam tomography (EBT) system in which an electron beam impinges upon a target ring at a beam spot that produces an x-ray fan beam detected by a plurality of detector arrays, said method comprising:

correlating changes in x-ray intensity for imaging elements of each detector array with deformations of the target ring during each imaging sweep of an initial activation of the EDT system;

estimating changes in a position of the electron beam on the target ring based on said correlating step;

deriving scale factors based on said estimating step; and modifying at least one of a trajectory and deflection of the electron beam during multiple imaging sweeps based on the derived scale factors for each imaging sweep to ensure that the corresponding beam spot maintains substantially the same angular positivn on the target ring, thereby ensuring that a resulting x-ray fan beam maintains the same position on the surfaces of the plurality of the detector arrays, through multiple imaging sweeps.

11. The method of claim 10, wherein said determining step further comprises estimating the change in radial position of the beam spot on the target ring using the following formulae:

$$\Delta_r = k(1 - \sqrt{(2(I_a/(I_b+I_a))}); \text{ and} \quad (1)$$

$$k = S(W/\tan \Theta)(C_s/C_d), \text{ where:} \quad (2)$$

$\Delta_r$=the change in the radial position of the beam spot;
$I_a$=the smaller of he two signals from the detector arrays;
$I_b$=the larger of the two signals from the detector arrays;
S=−1 if $I_a$ is on a first detector array, or 1 if $I_a$ is on a second detector array;
W=the detector exposure halfwidth;
Θ=the angle of a target ring with respect to a vertical plane;
$C_s$=the distance between a coillimator and the beam spot; and
$C_d$=the distance between the collimator and the detector arrays.

12. The method of claim 10, wherein said deriving step comprises deriving the scale factors using the following formula:

$$F = (R_s + D\Delta_r)/R_s, \text{ where:}$$

D=a dampening factor; and $R_s$=the radius of the beam spot for a particular sweep.

13. The method of claim 10, further comprising storing the scale factors for use in subsequent imaging procedures.

14. The method of claim 10, further comprising maintaining a uniform and constant x-ray intensity on each detector array through said modifying step.

15. The method of claim 10, wherein the x-ray intensity on each detector array is the same.

16. A method of stabilizing an x-ray source of an electron beam tomography (EBT) system in which an electron beam impinges upon a target ring at a beam spot that produces an x-ray fan beam detected by a plurality of detector arrays so that the x-ray intensity on each detector array is uniform through multiple imaging sweeps, said method comprising:

determining changes in x-ray intensity for detecting elements of each detector array through multiple imaging sweeps during an initial activation of the EBT system;

deriving scale factors based on the determined changes in x-ray intensity for the imaging sweeps; and using the scale factors to modify a trajectory and deflection of the electron beam during the multiple imaging sweeps to maintain constant x-ray intensities on each detector array.

17. The method of claim 16, wherein said determining step comprises correlating the changes in x-ray intensity for each detector array with a deformation of the target ring during each imaging sweep.

18. The method of claim 17, wherein said determining step further comprises determining a change in position of the electron beam on the target through the correlation of the deformation of the target ring.

19. The method of claim 18, wherein said determining step further comprises estimating the change in radius of the beam spot using the following formulae:

$$\Delta_r = k(1 - \sqrt{(2(I_a/(I_b + I_a))}); \text{ and} \quad (1)$$

$$k = S(W/\tan\Theta)(C_s/C_d), \text{ where:} \quad (2)$$

$\Delta_r$=the change in the radial position of the beam spot;

$I_a$=the smaller of the two signals from the detector arrays;

$I_b$=the larger of the two signals from the detector arrays;

S=−1 if $I_a$ is on a first detector array, or 1 if $I_b$ is on a second detector array;

W=the detector exposure halfwidth;

Θ=the angle of a target ring with respect to a vertical plane;

$C_s$=the distance between a collimator and the beam spot; and $C_d$=the distance between the collimator and the detector arrays.

20. The method of claim 19, wherein said deriving step comprises deriving the scale factors using the following formula:

$$F = (R_s + D\Delta_r)/R_s,$$

where:

D=a dampening factor; and $R_s$=the radius of the beam spot for a particular sweep.

21. The method of claim 16, further comprising storing the scale factors for use in subsequent imaging procedures.

22. The method of claim 16, wherein the scale factors are different for each imaging sweep.

23. The method of claim 16, wherein the x-ray intensities on the detecting elements of each detector array are the same due to said using step.

* * * * *